United States Patent
Mirza et al.

(10) Patent No.: US 11,472,617 B2
(45) Date of Patent: Oct. 18, 2022

(54) **BIODEGRADABLE BOTTLE CAP USING *PESTALOTIOPSIS MICROSPORIA* TO BIODEGRADE WASTE PLASTIC BOTTLE**

(71) Applicants: Faizan Mirza, Irving, TX (US); Hana Ahmad, Allen, TX (US); Humza Ahmad, Allen, TX (US); Mohsen Ahmad, Allen, TX (US); Rabiya Sayeed, Murphy, TX (US); Sofia Ali, Garland, TX (US); Zain Ali, Garland, TX (US); Sarah Nawab, Dallas, TX (US); Danyal Nawab, Dallas, TX (US); Rizwan Mirza, Patna (IN)

(72) Inventors: Faizan Mirza, Irving, TX (US); Hana Ahmad, Allen, TX (US); Humza Ahmad, Allen, TX (US); Mohsen Ahmad, Allen, TX (US); Rabiya Sayeed, Murphy, TX (US); Sofia Ali, Garland, TX (US); Zain Ali, Garland, TX (US); Sarah Nawab, Dallas, TX (US); Danyal Nawab, Dallas, TX (US); Rizwan Mirza, Patna (IN)

(73) Assignee: INNOWAYTORS LLC

( * ) Notice: Subject to any disclaimer, the term of this patent is extended or adjusted under 35 U.S.C. 154(b) by 411 days.

(21) Appl. No.: 16/575,925

(22) Filed: Sep. 19, 2019

(65) Prior Publication Data
US 2021/0086970 A1   Mar. 25, 2021

(51) Int. Cl.
| | | |
|---|---|---|
| B65D 65/46 | (2006.01) | |
| C12N 1/14 | (2006.01) | |
| A61K 36/06 | (2006.01) | |

(52) U.S. Cl.
CPC ............ *B65D 65/466* (2013.01); *A61K 36/06* (2013.01); *C12N 1/14* (2013.01); *C08L 2201/06* (2013.01)

(58) Field of Classification Search
CPC ........ B65D 51/00; B65D 51/18; B65D 51/20; B65D 51/22; B65D 51/228; B65D 65/46; B65D 65/466; A61K 36/06; Y02W 90/10; C08K 2201/018; B65F 2250/105; B65F 55/10; B65F 55/14; C08L 2201/06
USPC ......... 428/34.1, 35.7, 35.8, 35.2, 35.3, 36.9, 428/63.91, 36.92; 215/316–354; 206/527
See application file for complete search history.

(56) References Cited

U.S. PATENT DOCUMENTS

2008/0041810 A1*  2/2008  Itoh .................... B65D 41/3428
                                                 215/316
2020/0317419 A1* 10/2020  Johnson ............... B65D 85/187

* cited by examiner

*Primary Examiner* — Lee E Sanderson

(57) ABSTRACT

Millions of plastic water bottles going to waste and harming the environment. Recycling is an option, but hardly becoming a practice. Biodegradable bottle cap consisting of the plastic-eating fungus 'pestalotiopsis microsporia', will consumes the plastic bottle and the cap so no trace is left behind. The cap is made of plastic and the fungus is contained in an aluminium casing.

3 Claims, 2 Drawing Sheets

Various sections of the top cover of the bottle cap

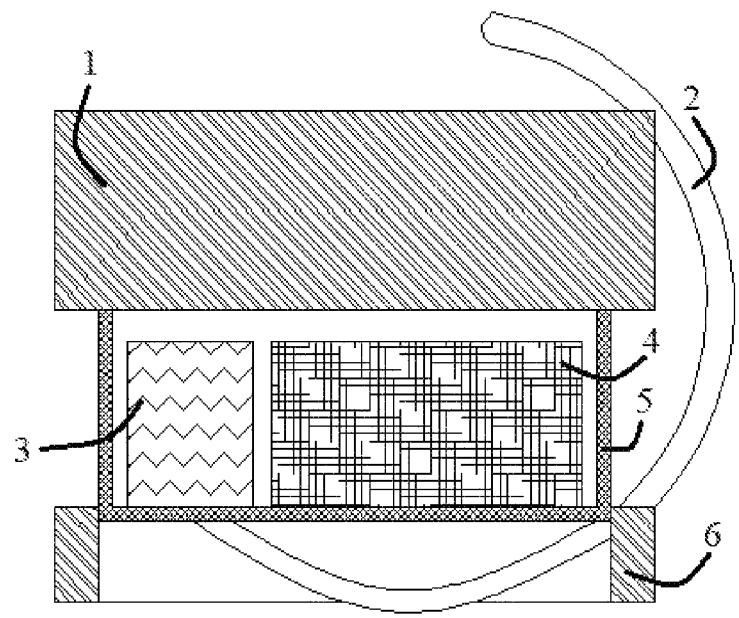
FIG 1: Various sections of the top cover of the bottle cap
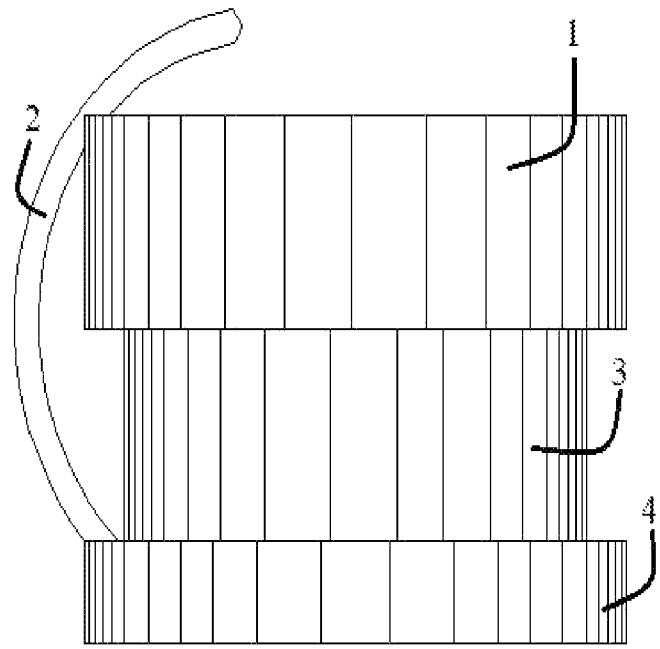
FIG 2: Side view of the top part layers of the cap

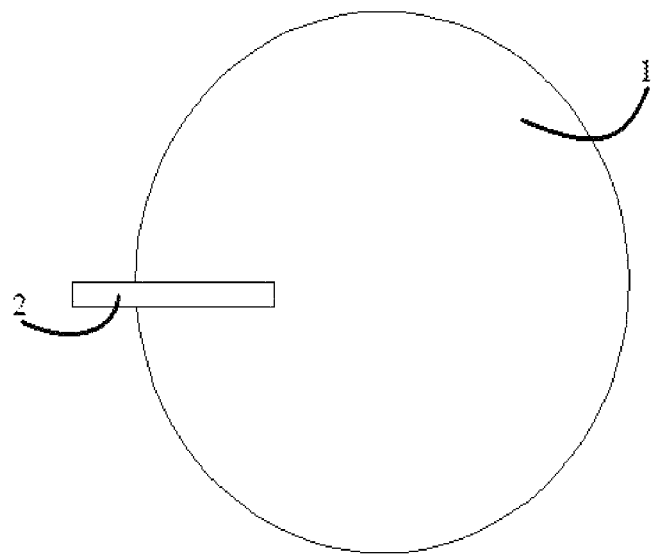
FIG 3: The outer shell of the biodegradable cap
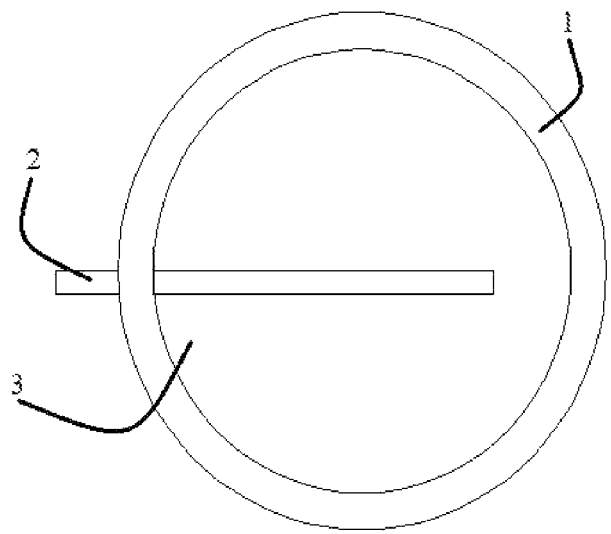
FIG 4: The outer shell of the cap as seen from above

BIODEGRADABLE BOTTLE CAP USING *PESTALOTIOPSIS MICROSPORIA* TO BIODEGRADE WASTE PLASTIC BOTTLE

BACKGROUND OF THE INVENTION

Millions of plastic water bottles going to waste and harming the environment. Recycling is an option, but only 23% of Americans recycle plastic. Ooho drinking capsule was invented to solve this problem, but it is made of algae and therefore more fragile than plastic. Moreover, Ooho was to destroy the plastic industry and did not turn out to be successful. Biodegradable bottle cap using 'pestalotiopsis microsporia' allows for the continued use of plastic without the plastic going to waste and harming environment.

TECHNICAL FIELD

Plastic bottle cap consisting of the plastic-eating fungus 'pestalotiopsis microsporia' will be used to the reduction of plastic-bottle waste generated after the use of the packaged drinking water bottles through biodegradation. The bottle is expected to be biodegraded by plastic-eating fungus 'pestalotiopsis microsporia' in few weeks' time instead of hundreds of years.

INVENTION SUMMARY

Biodegradable bottle cap is a water bottle cap containing the plastic eating fungus pestalotiopsis microsporia. When the consumer is done drinking from the bottle, the cap has a tab that is pulled and this tab releases the fungus. The fungus consumes the plastic bottle and the cap so no trace is left behind. The cap is made of plastic and the fungus is contained in an aluminium casing. Also contain in the casing is the safe food dye which will be colouring the water in case of accidental release or opening of the casing before the use of the drinking water. Such water colouring will be an indication to avoid using the water for drinking though the fungus is safe after human galloping.

BRIEF DESCRIPTIONS OF THE DRAWINGS

FIG. 1 is the various sections of the top cover of the bottle cap.

FIG. 2 is the side view of the top part layers of the cap.

FIG. 3 is the outer shell of the biodegradable cap.

FIG. 4 is the outer shell of the cap as seen from above.

DETAILED DESCRIPTIONS OF THE DRAWINGS

FIG. 1 is the bottle cap's top cover and section 1 protects the components of the cap and is made of plastic. Section 2 is the pull able tab, when it is pulled, it breaks the barrier separating the fungus and the rest of the cap, causing the fungus to consume the plastic bottle. At the same time, the tab locks the bottle so it can no longer be opened, so when the consumer is done drinking the water, they need to put the cap back on in order for the fungus to consume the bottle. Section 3 is where the food coloring is stored. When the tab breaks it open, the food coloring is released along with the fungi. Section 4 is the space where the fungi are stored. It is in the aluminium casing because so that it cannot eat through the bottle early. When the tab is pulled the fungi is released with the food coloring. Section 5 is the aluminium casing. It contains both the fungi and the food coloring. Aluminium is environmentally friendly, so it will contain the fungi prior to release. Section 6 is the bottom level of the cap. It is made of plastic and it can be opened by pulling the tab. This is the start of the process of the fungi's consumption of the bottle.

FIG. 2 is the top part layer of the cap where 1 is a protection for the top of the cap and it biodegrades with the rest of the cap. 2 is the pull able tab that pulls out the aluminium that is supporting the fungus. Upon being pulled, the tab drops the fungus into the bottle. 3 is the plastic shell of the aluminium compartment containing the fungi and the food coloring. 4 is the bottom layer of the cap. When the tab is pulled, it serves as a trapdoor for the fungus to be released into the bottle.

FIG. 3 is the outer shell of biodegradable cap. It is made of plastic which will biodegrade upon the fungi's release. 2 is the tab system. When the bottle use has finished, the tab will be pulled and it will lock into place and the bottle cannot open.

FIG. 4 is the outer shell as seen from above made of plastic. 2 is the lock system as seen from above. It is to lock the bottle in place after the fungus pestalotiopsis microsporia has been released. When the tab is pulled, it will lock in place so the bottle cannot open. 3 is the inner shell made of aluminium and holds the fungus prior to their release. It is of aluminium because it is not that bad for the environment and if it were plastic, the fungus would eat through it too early.

DETAILED DESCRIPTION OF THE INVENTION

To initiate the biodegradation of used plastic bottle having biodegradable bottle cap using 'pestalotiopsis microsporia' fixed on the bottle, all that is required is to pull the tab coming out of the bottle cap. When the tab is pulled, which is connected to the aluminium casing separating the fungi from the bottle content, the tab will break the aluminium seal. The breaking of the seal after the bottle content being used, releases the fungi into the bottle to biodegrade it.

In the case of accidental brokerage of the seal during the filled bottle content the red food coloring stored along with fungus will indicate the brokerage as it will show the red color water after mixing with the content of the bottle. This will let people know that the water is not safe to drink. The cap is round, the ideal shape of a cap, and is made out of plastic from the outside. The bottle itself will be 22 cm tall, (being able to hold about 16.9 fluid ounces), with the plastic part of the cap having a diameter of approximately 2.5 centimetres and a height of 2 centimetres.

Inside the cap, there will be an aluminium casing that contains the plastic-consuming fungi. This aluminium casing will have a diameter of an estimated 2 centimetres and a height of 0.8 centimetres. The casing will keep the fungi from consuming the plastic outer layer of the cap. The cap also consists of a tab, in which one of the ends will be attached to the base of the aluminium casing. Part of the tab will protrude outside from the inside of the cap. When the tab is pulled, it will break the bottom seal of the aluminium casing, allowing the fungi to be released into the empty bottle for disposal. The fungi will fully consume the plastic within a matter of weeks. In the bottle, the cap is 3 times as high with about the same diameter as an ordinary bottle cap, to be able to contain the fungi and food dye. The invention could also have different types of colors of food dye. It can also use other materials to case the fungi.

The invention claimed is:

1. A cap for a plastic bottle, wherein the cap comprises an inside and an outside, and
   wherein disposed within the inside of the cap is a casing formed from an aluminum or other solid substance, said casing containing the fungus Pestalotiopsis microsporia, and
   wherein the casing comprises a pull tab which is configured to release the Pestalotiopsis microsporia when pulled.

2. The cap of according to claim 1, wherein the casing additionally contains a food dye or colored liquid, wherein the casing is configured to release the food dye or colored liquid when the pull tab is pulled.

3. The cap according to claim 2, wherein the casing containing the food dye or colored liquid and the Pestalotiopsis microsporia comprises a solid metal clip which locks the cap thereby preventing the cap from being used again, and
   wherein the casing is configured such that when the pull tab is pulled the food dye or colored liquid and the Pestalotiopsis microsporia are released together.

* * * * *